(12) United States Patent
Brandt et al.

(10) Patent No.: US 6,696,067 B2
(45) Date of Patent: Feb. 24, 2004

(54) COSMETIC COMPOSITIONS CONTAINING DISPERSION POLYMERS

(75) Inventors: Loralei Marie Brandt, Cary, IL (US); Douglas E. Betts, Warrenville, IL (US); Cathy C. Johnson, Geneva, IL (US)

(73) Assignee: Ondeo Nalco Company, Naperville, IL (US)

( * ) Notice: Subject to any disclaimer, the term of this patent is extended or adjusted under 35 U.S.C. 154(b) by 0 days.

(21) Appl. No.: 09/834,128

(22) Filed: Apr. 12, 2001

(65) Prior Publication Data

US 2003/0059382 A1 Mar. 27, 2003

(51) Int. Cl.⁷ .............................. A61K 6/00; A61K 7/00; A61K 7/04; A61K 7/06; A61K 47/30
(52) U.S. Cl. .................... 424/401; 424/61; 424/70.1; 514/844; 514/845; 514/772.3
(58) Field of Search .............................. 424/401, 78.08, 424/70.1, 61; 514/844, 845, 772.3

(56) References Cited

U.S. PATENT DOCUMENTS

| | | |
|---|---|---|
| 4,333,924 A | 6/1982 | Bowley et al. |
| 4,760,096 A | 7/1988 | Sakai et al. |
| 4,952,391 A | 8/1990 | Lang et al. |
| 5,013,763 A | 5/1991 | Tubesing et al. |
| 5,034,219 A | 7/1991 | Deshpande et al. |
| 5,277,899 A * | 1/1994 | McCall .................. 424/71 |
| 5,338,541 A * | 8/1994 | Matz et al. .............. 424/71 |
| 5,804,205 A | 9/1998 | Epstein et al. |
| 6,066,326 A | 5/2000 | Afriat et al. |
| 6,265,477 B1 * | 7/2001 | Hurlock ................ 524/458 |

FOREIGN PATENT DOCUMENTS

| | | |
|---|---|---|
| EP | 197 649 | 10/1986 |
| EP | 522 756 | 1/1993 |
| WO | WO 02/41856 | 3/2002 |

OTHER PUBLICATIONS

U.S. application Ser. No. 09/730,936, Melby.

* cited by examiner

*Primary Examiner*—Thurman K. Page
*Assistant Examiner*—S. Howard
(74) *Attorney, Agent, or Firm*—Michael B. Martin; Thomas M. Breininger

(57) ABSTRACT

A cosmetically acceptable composition for treating hair, skin and nails comprising from about 0.001 to about 25 weight percent, based on polymer solids, of a stable dispersion in an aqueous salt solution of a cationic, anionic or nonionic polymer having a weight average molecular weight of from about 10,000 to about 50,000,000 and a method of treating hair, skin or nails are disclosed.

12 Claims, No Drawings

US 6,696,067 B2

COSMETIC COMPOSITIONS CONTAINING DISPERSION POLYMERS

TECHNICAL FIELD

This invention relates to novel compositions for use in personal care formulations and applications. More particularly, this invention relates to cosmetic compositions comprising cationic, anionic or nonionic dispersion polymers, to methods of preparing the compositions and to methods of using the compositions to treat keratinous substrates such as hair, skin and nails.

BACKGROUND OF THE INVENTION

The surface properties of human hair, skin and nails are of basic interest in cosmetic science, and there has thus been a long-standing desire to discover cosmetic compositions which will beneficially affect the topical and bulk condition of these keratinous substrates. Such compositions should have adequate adherent properties, so that they are not only absorbed initially, but are also retained on exposure to water. This ability to be absorbed onto the substrate and to resist water rinse off is referred to as substantivity.

Compositions for treating hair should improve the wet and dry combability of the hair, facilitate detangling in wet hair combing and reduce static flyaway in dry hair combing while also imparting softness and suppleness to the hair. Ingredients used in shampoos should impart improved foam stability to the shampoo while hair fixative compositions should impart properties such as good curl retention without having a deleterious effect on wet combability.

With respect to compositions for treating skin, compositions are desired which will function to improve such properties as retention of skin moisture, softening of the skin, attraction of air moisture, retardation of skin water loss, feel and reduction of skin irritations caused by contact with detergents, soaps and the like. Compositions for treating nails should strengthen or harden fragile or brittle nails and improve the overall appearance of the nails.

It is, therefore, an object of this invention to develop new cosmetic compositions having the above beneficial properties for treating hair, skin and nails.

SUMMARY OF THE INVENTION

In its principal aspect, this invention is directed to a cosmetically acceptable composition for treating hair, skin and nails comprising from about 0.001 to about 25 weight percent, based on polymer solids, of a stable dispersion in an aqueous salt solution of a cationic, anionic or nonionic polymer having a weight average molecular weight of from about 10,000 to about 50,000,000 g/mol.

In another aspect, this invention is directed to a method of treating hair, skin or nails comprising applying to the hair, skin or nails a cosmetically acceptable composition comprising from about 0.001 to about 25 weight percent, based on polymer solids, of a stable dispersion in an aqueous salt solution of a cationic, anionic or nonionic polymer having a weight average molecular weight of from about 10,000 to about 50,000,000 g/mol.

DETAILED DESCRIPTION OF THE INVENTION

Definitions of Terms

As used herein, the following abbreviations and terms shall have the following meanings.

"AA" for Acrylic Acid.
"AcAm" or "Am" for acrylamide.
"AMP" for amino methyl propane.
"DADMAC" for diallyldimethylammonium chloride.
"DEA" for diethanolamide
"DMAEA" for dimethylaminoethyl acrylate.
"DMAEM" for dimethylaminoethyl methacrylate.
"DMAEA•BCQ" or "BCQ" for dimethylaminoethyl acrylate, benzyl chloride quaternary salt.
"DMAEA•MCQ" or "MCQ" for dimethylaminoethyl acrylate, methyl chloride quaternary salt.
"MAPTAC" for methacrylamidopropyltrimethylammonium chloride.
"MEA" for monoethanolamide.
"NF" for National Formulary.
"PABA" for p-Amino benzoic acid.
"PCA" for percarboxlic acid.
"PVM/MA" for Polymethyl vinyl ether/maleic anhydride.
"PVP" for polyvinyl pyrrolidone.
"USP" for United States Pharmacopia.
"VA" for vinyl acetate.
"Alkyl" means a monovalent group derived from a straight or branched chain saturated hydrocarbon by the removal of a single hydrogen atom. Representative alkyl groups include methyl, ethyl, n- and iso-propyl, and the like.
"Alkylene" means a divalent group derived from a straight or branched chain saturated hydrocarbon by the removal of two hydrogen atoms. Representative alkylene groups include methylene, ethylene, propylene, and the like.
"Alkoxy" and "alkoxyl" mean an alkyl-O-group wherein alkyl is defined herein. Preferred alkoxy are $C_1$–$C_4$ alkyl-O-groups. Representative alkoxy groups include methoxy, ethoxy, propoxy, butoxy, and the like.
"Anionic monomer" means a monomer as defined herein which possesses a net negative charge. Representative anionic monomers include acrylic acid, and it's salts, including, but not limited to sodium acrylate, and ammonium acrylate, methacrylic acid, and it's salts, including, but not limited to sodium methacrylate, and ammonium methacrylate, 2-acrylamido-2-methylpropanesulfonic acid (AMPS), the sodium salt of AMPS, sodium vinyl sulfonate, styrene sulfonate, maleic acid, and it's salts, including, but not limited to the sodium salt, and ammonium salt, sulfonate itaconate; sulfopropyl acrylate or methacrylate or other water-soluble forms of these or other polymerisable carboxylic or sulphonic acids. Sulfomethylated acrylamide, allyl sulfonate, sodium vinyl sulfonate, itaconic acid, acrylamidomethylbutanoic acid, fumaric acid, vinylphosphonic acid, vinylsulfonic acid, allylphosphonic acid, sulfomethylated acryamide, phosphonomethylated acrylamide, and the like.
"Aryl" means an aromatic monocyclic or multicyclic ring system of about 6 to about 10 carbon atoms. The aryl is optionally substituted with one or more $C_1$–$C_{20}$ alkyl, alkoxy or haloalkyl groups. Representative aryl groups include phenyl or naphthyl, or substituted phenyl or substituted naphthyl.
"Arylalkyl" means an aryl-alkylene-group where aryl and alkylene are defined herein. Representative arylalkyl groups include benzyl, phenylethyl, phenylpropyl, 1-naphthylmethyl, and the like. Benzyl is preferred.
"Cationic Monomer" means a monomer as defined herein which possesses a net positive charge. Representative cationic monomers include dialkylaminoalkyl acrylates and methacrylates and their quaternary or acid salts, including, but not limited to, dimethylaminoethyl acrylate methyl chloride quaternary salt, dimethylaminoethyl acrylate methyl sulfate quaternary salt, dimethyaminoethyl acrylate benzyl chloride quaternary salt, dimethylaminoethyl acrylate sulfuric acid salt, dimethylaminoethyl acrylate hydrochloric acid salt, diethylaminoethyl acrylate, methyl chloride quaternary salt, dimethylaminoethyl methacrylate methyl chloride quaternary salt, dimethylaminoethyl methacrylate methyl sulfate quaternary salt, dimethylaminoethyl methacrylate benzyl chloride quaternary salt, dimethylaminoethyl methacrylate sulfuric acid salt, dimethylaminoethyl methacrylate hydrochloric acid salt, dimethylaminoethyl methacryloyl hydrochloric acid salt, dialkylaminoalkylacrylamides or methacrylamides and their quaternary or acid salts such as acrylamidopropyltrimethylammonium chloride, dimethylaminopropyl acrylamide methyl sulfate quaternary salt, dimethylaminopropyl acrylamide sulfuric acid salt, dimethylaminopropyl acrylamide hydrochloric acid salt, methacrylamidopropyltrimethylammonium chloride, dimethylaminopropyl methacrylamide methyl sulfate quaternary salt, dimethylaminopropyl methacrylamide sulfuric acid salt, dimethylaminopropyl methacrylamide hydrochloric acid salt, diethylaminoethylacrylate, diethylaminoethylmethacrylate and diallyldialkylanumonium halides such as diallyldiethylammonium chloride and diallyldimethyl ammonium chloride.

"Cycloalkyl" means a non-aromatic mono- or multicyclic ring system of about 5 to about 10 carbon atoms. Preferred ring sizes of rings of the ring system include about 5 to about 6 ring atoms. The cycloalkyl is optionally substituted with one one or more substituents selected from alkyl, alkoxy and haloalkyl. Representative monocyclic cycloalkyl include cyclopentyl, cyclohexyl, cycloheptyl, and the like. Representative multicyclic cycloalkyl include 1-decalin, norbornyl, adamant-(1- or 2-)yl, and the like.

"Dispersion polymer" polymer means a water-soluble polymer dispersed in an aqueous continuous phase containing one or more inorganic salts. Representative examples of dispersion polymerization of water-soluble polymers in an aqueous continuous phase can be found in U.S. Pat. Nos. 5,605,970; 5,837,776; 5,985,992; 4,929,655; 5,006,590; 5,597,859; and 5,597,858 and in European Patent Nos. 183,466; 657,478; and 630,909.

Dispersion polymers are prepared by combining water, one or more inorganic salts, one or more water-soluble monomers, any polymerization additives such as chelants, pH buffers or chain transfer agents, and a water-soluble stabilizer polymer. In addition, further processing, structure modifying and/or stabilizing agents may be added to the mixture. All or a portion of this mixture is charged to a reactor equipped with a mixer, thermocouple, nitrogen purging tube, and water condenser. The solution is mixed vigorously, heated to the desired temperature, and then a water-soluble initiator is added. The solution is purged with nitrogen while maintaining temperature and mixing for several hours. During the course of the reaction, a discontinuous phase containing the water-soluble polymer is formed. A portion of the reaction mixture containing any combination of the starting materials may be added in a semi-batch fashion during the course of the polymerization to improve processing or affect polymer composition or molecular weight. After this time, the products are cooled to room temperature, and any post-polymerization additives are charged to the reactor. Water continuous dispersions of water-soluble polymers are free flowing liquids with product viscosities of from about 50 to about 10,000 centipoise (cP), as measured at low shear.

Inorganic salts suitable for preparing the dispersion polymer include inorganic or organic sulfates, phosphates, chlorides, fluorides, citrates, acetates, tartrates, hydrogenphosphates or a mixture thereof. Preferred salts include ammonium sulfate, sodium sulfate, magnesium sulfate, aluminum sulfate, ammonium hydrogen phosphate, sodium hydrogen phosphate, potassium hydrogen phosphate, sodium chloride and ammonium chloride. The salts are used in aqueous solution typically having a combined total concentration of 15 weight percent or above in the product mixture.

Additional cationic salts which may be used alone or in combination with the above inorganic salts for preparing anionic dispersion polymers. Preferred cationic salts include tetraalkylammonium halides having from 4 to 22 carbon atoms, substituted tetraalkylammonium halides having from 4 to 22 carbon atoms, aryl trialkylammonium halides having from 9 to 22 carbon atoms, and substituted aryl trialkylammonium halides having from 9 to 22 carbon atoms are preferred. Representative preferred cationic salts include cetylpyridinium chloride, cetylmethylammonium chloride and benzyltriethylammonium chloride.

Cationic dispersion polymers may also be prepared using a mixture of the inorganic salts described above with one or more anionic inorganic salts and one or more thiocyanates, perchlorates, chlorates, bromides, iodides or nitrates, including sodium, potassium or ammonium thiocyanate, sodium perchlorate, sodium chlorate, sodium bromide, sodium iodide, sodium nitrate and the like.

Representative anionic salts include metal or ammonium salts of trichloroacetate and trifluoromethanesulfonate; sulfonates and disulfonates such as methanesulfonate, ethanesulfonate, propanesulfonate, butanesulfonate, butanedisulfonate, pentanesulfonate, hexanesulfonate, hexanedisulfonate, and octanedisulfonate; aryl and substituted aryl sulfonates and disulfonates such as benzenesulfonate, nitrobenzenesulfonate, xylenesulfonate, toluenesulfonate, benzenedisulfonate, naphthalenesulfonate; dialkylsulfosuccinates such as diisobutylsulfosuccinate, diisooctylsulfosuccinate, dimethylsulfosuccinate, diethylsulfosuccinate, and diisopropylsulfosuccinate; dicycloalkylsulfosuccinates; and diarylsulfosuccinates. Preferred anionic salts include sodium hexanesulfonate, sodium benzenesulfonate, sodium xylenesulfonate sodium benzenedisulfonate, sodium butanedisulfonate, sodium hexanedisulfonate, sodium octanedisulfonate, and sodium decanedisulfonate. The relatively hydrophobic nature of these salts facilitate dispersion formation. Such salts may be added in any order with the other reaction components, and the order of addition can be used to effect changes in polymer processing.

Suitable polymeric stabilizing agents for preparing cationic and nonionic dispersion polymers include watersoluble cationic polymers that are preferably soluble in the aqueous salt solution. The dispersant is used in an amount of from about 1 to about 10% by weight based on the total weight of the dispersion polymer. The polymeric stabilizing agents or stabilizers facilitate discrete particle formation and prevent agglomeration and gel formation.

Suitable cationic stabilizers for preparing cationic and nonionic dispersion polymers include but are not limited to homopolymers of cationic diallyl-N,N-disubstituted ammonium monomers, homopolymers of N,N-disubstituted-aminoethyl(meth)acrylate monomers and their quaternary salts, homopolymers of N,N-disubstituted-aminopropyl (meth)acrylamide and their quaternary salts, copolymers of diallyl-N,N-disubstituted ammonium monomers and N,N-disubstituted-aminoethyl(meth)acrylate monomers and their quaternary salts, copolymers of diallyl-N,N-disubstituted ammonium monomers and N,N-disubstituted-aminopropyl (meth)acrylamide monomers and their quaternary salts and cationic polymers comprising at least 20 mole percent of one or more cationic diallyl-N,N-disubstituted ammonium monomers, N,N-disubstituted-aminoethyl(meth)acrylate monomers and their quaternary salts or N,N-disubstituted-aminopropyl(meth)acrylamide monomers and their quaternary salts and one or more nonionic monomers, preferably (meth)acrylamide, N-substituted or N,N-disubstituted (meth)acrylamide or styrene, and mixtures thereof. The molecular weight of the stabilizer is preferably in the range of about 10,000 to 10,000,000 g/mol.

Stabilizers used for preparing anionic and nonionic dispersion polymers include anionically charged water soluble polymers having a molecular weight of from about 10,000 to about 10,000,000 and preferably from about 1,000,000 to about 3,000,000. The stabilizer polymer must be soluble or slightly soluble in the salt solution, and must be soluble in water.

Representative anionic stabilizers include but are not limited to polyacrylic acid, poly(meth)acrylic acid, poly(2-acrylamido-2-methyl-1-propanesulfonic acid), copolymers of 2-acrylamido-2-methyl-1-propanesulfonic acid and an anionic comonomer selected from acrylic acid and methacrylic acid, polymers of one or more anionic monomers and one or more nonionic monomers, and the sodium salts of the aforementioned anionic stablizers.

Nonionic dispersants can also be used alone or in combination with the cationic, anionic and nonionic stabilizers described herein for preparing cationic, anionic and non-ionic dispersion polymers. Representative nonionic dispersants include, but are not limited to polyvinyl alcohol, polyvinyl pyrrolidinone, polyethylene glycol, polypropylene glycol, polyethylene oxide, polyethylene, soluble starch, epichlorohydrin/dimethylamine, poly(N-vinylpyridine), and the like.

A multifunctional alcohol such as glycerin or ethylene glycol may also be included in the polymerization system. The deposition of the fine particles is smoothly carried out in the presence of these alcohols.

The polymerization reaction is initiated by any means that results in generation of a suitable free radical. Initiation may be induced through the use of any number of conventional systems including thermal, photochemical, or redox coupled initiation systems. Thermally derived radicals, in which the radical species results from thermal, homolytic dissociation of a water-soluble azo, peroxide, hydroperoxide and perester compound are preferred. Especially preferred initiators are azo compounds including 2,2'-azobis(2-amidinopropane) dihydrochloride and 2,2'-azobis(N,N'-dimethyleneisobutylamine) hydrochloride, and the like.

A seed polymer may be added to the reaction mixture before the initiating polymerization of the monomers for the purpose of facilitating a fine dispersion of particles. The seed polymer is a water-soluble polymer insoluble in the aqueous solution of the polyvalent anionic salt. The monomer composition of the seed polymer need not be identical to that of the water-soluble polymer formed during polymerization. The seed polymer is preferably a polymer prepared by the dispersion polymer process described herein.

Since the dispersion polymers do not contain surfactants or oil, the dispersion polymers are environmentally friendly. Moreover, the absence of oil in the dispersion polymers equates to such polymers having virtually zero volatile organic content (VOC), and dramatically reduced biological oxygen demand (BOD), carbon oxygen demand (COD) and total organic carbon (COD) compared to conventional inverse emulsion polymers. This is another environmental advantage of such polymers.

"Halogen" and "halo" mean fluorine, chlorine, bromine or iodine.

"Haloalkyl" means an alkyl group, as defined herein, having one, two, or three halogen atoms attached thereto. Representative haloalkyl groups include chloromethyl, bromoethyl, trifluoromethyl, and the like.

"Hydrophobic cationic monomer" means a monomer of formula

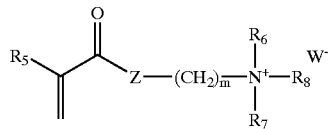

where $R_5$ is H or $CH_3$; $R_6$, $R_7$ and $R_8$ are independently selected from H, $CH_3$, $CH_2CH_3$, aryl, arylalkyl, $C_6$–$C_{20}$ alkyl and $C_5$–$C_{10}$ cycloalkyl; $R_9$ is aryl, $C_6$–$C_{20}$ alkyl or alkoxy; m is 2 or 3; Z is O or NH; and W is Cl, Br, I, $CH_3OSO_3$, $CH_3CO_2$, $HSO_4$, $HPO_4$, $R_9CO_2$ or $R_9SO_3$, provided that when all of $R_6$, $R_7$ and $R_8$ are H, $CH_3$ or $CH_2CH_3$, W is $R_9CO_2$ or $R_9SO_3$. A hydrophobic cationic monomer is less water soluble than a hydrophilic cationic monomer as defined above, and contains alkyl or aromatic groups which confer this property.

Preferred hydrophobic cationic monomers are those where $R_6$ and $R_7$ are independently selected from H, $CH_3$, $CH_2CH_3$; $R_8$ is selected from aryl, arylalkyl, $C_6$–$C_{20}$ alkyl and $C_5$–$C_{10}$ cycloalkyl; and W is selected from Cl, Br, I, $CH_3OSO_3$, $CH_3CO_2$; $HSO_4$ and $HPO_4$.

Other preferred hydrophobic cationic monomers are those where $R_6$, $R_7$ and $R_8$ are independently selected from H, $CH_3$ and $CH_2CH_3$; and W is $R_9CO_2$ or $R_9SO_3$.

"(Meth)acrylic acid" means acrylic acid or methacrylic acid or a salt thereof.

"(Meth)acrylamide" means acrylamide or methacrylamide.

"Monomer" means a polymerizable allylic, vinylic or acrylic compound. The monomer may be anionic, cationic, nonionic or zwitterionic. Vinyl monomers are preferred, acrylic monomers are more preferred. "Nonionic monomer" means a monomer as defined herein which is electrically neutral. Representative non-ionic, water-soluble monomers include acrylamide, methacrylamide, N-methylacrylamide, N,N-dimethylacrylamide, N,N-diethylacrylamide, N-isopropylacrylamide, N-vinylformamide, N-vinylmethylacetamide, dimethylhydroxypropyl (meth) acrylate, hydroxyethyl methacrylate, hydroxyethyl acrylate, hydroxypropyl acrylate, hydroxypropyl methacrylate, N-t-butylacrylamide, N-methylolacrylamide, vinyl acetate, acrylonitrile, 2-ethylhexyl acrylate, and the like.

"RSV" stands for Reduced Specific Viscosity. Within a series of polymer homologs which are substantially linear and well solvated, "reduced specific viscosity (RSV)" measurements for dilute polymer solutions are an indication of polymer chain length and average molecular weight according to Paul J. Flory, in "*Principles of Polymer Chemistry*", Cornell University Press, Ithaca, N.Y., © 1953, Chapter VII, "*Determination of Molecular Weights*", pp. 266–316. The RSV is measured at a given polymer concentration and temperature and calculated as follows:

$$RSV = \frac{[(\eta/\eta_0) - 1]}{c}$$

η=viscosity of polymer solution
η₀=viscosity of solvent at the same temperature
c=concentration of polymer in solution.

The units of concentration "c" are (grams/100 ml or g/deciliter). Therefore, the units of RSV are dl/g. In this patent application, a 1.0 or 0.125 molar sodium nitrate solution is used for measuring RSV. The polymer concentration in this solvent is measured at about 0.045 g/dL. The RSV is measured at 30° C. The viscosities η and η are measured using a Cannon Ubbelohde semimicro dilution viscometer, size 75. The viscometer is mounted in a perfectly vertical position in a constant temperature bath adjusted to 30±0.02° C. The error inherent in the calculation of RSV is about 2 dl/grams. When two polymer homologs within a series have similar RSV's that is an indication that they have similar molecular weights.

Preferred Embodiments

Representative polymer dispersions suitable for use in preparing the cosmetically acceptable compositions of this invention are listed in Table 1. The polymer dispersions are available from ONDEO Nalco, Naperville, Ill.

TABLE 1

Properties of Representative Dispersion Polymers

| Composition (mole percent) | Brookfield Viscosity (spindle 3, 12 rpm) cps | RSV dL/g | Percent Solids |
|---|---|---|---|
| 90:10 Am/MCQ | 325 | 0.6 | 20 |
| 90:10 Am/MCQ | 350 | 2.2 | 20 |
| 90:10 Am/MCQ | 475 | 3.5 | 20 |
| 90:10 Am/MCQ | NA | 16 | 20 |
| 90:10 Am/BCQ | NA | 19.3 | 15 |
| 65:15:20 Am/BCQ/MCQ | 1150 | 3 | 20 |
| 65:15:20 Am/BCQ/MCQ | 575 | 0.5 | 20 |
| 65:15:20 Am/BCQ/MCQ | 1850 | 3.5 | 20 |
| 65:25:10 Am/BCQ/MCQ | NA | 16–21 | 20 |
| 65:25:10 Am/BCQ/MCQ | NA | 30 | 20 |
| 70:30 Am/DADMAC | 700 | 3 | 20 |
| 70:30 Am/DADMAC | 650 | 0.6 | 20 |
| 70:30 Am/DADMAC | 770 | 3.6 | 20 |
| 70:30 Am/DADMAC | NA | 4–5 | 20 |
| 20:50:30 Am/BCQ/MCQ | NA | 16–18 | 20 |
| 20:50:30 Am/BCQ/MCQ | NA | 11.8 | 25 |
| 20:50:30 Am/BCQ/MCQ | 810 | 3.9 | 25 |
| 20:50:30 Am/BCQ/MCQ | 770 | 0.6 | 25 |
| 20:50:30 Am/BCQ/MCQ | 400 | 0.4 | 25 |
| 50:17:33 Am/BCQ/MCQ | 1900 | 0.7 | 25 |
| 70:30 Am/AA | NA | 30 | 25 |
| 93:7 Am/AA | NA | 23 | 15 |
| 100 Am | 488 | NA | 20 |

In a preferred aspect of this invention, the cationic, anionic or nonionic polymer has a weight average molecular weight of from about 100,000 to about 30,000,000 g/mol.

In another preferred aspect, the cosmetically acceptable composition comprises from 0.01 to about 5 weight percent, based on polymer solids, of the cationic, anionic or nonionic polymer.

In another preferred aspect, the cosmetically acceptable composition comprises a stable dispersion in an aqueous salt solution of a cationic copolymer comprising from about 5 to about 95 mole percent diallyldimethylammonium chloride and from about 95 to about 5 mole percent acrylamide, wherein the dispersion has an RSV from about 0.4 to about 12 dL/g.

In another preferred aspect, the cosmetically acceptable composition comprises a stable dispersion in an aqueous salt solution of a cationic terpolymer comprising from about 5 to about 90 mole percent acrylamide, from about 5 to about 90 mole percent dimethylaminoethyl acrylate benzyl chloride quaternary salt and from about 5 to about 90 mole percent dimethylaminoethyl acrylate methyl chloride quaternary salt wherein the dispersion has an RSV from about 0.4 to about 30 dL/g.

In another preferred aspect, the cosmetically acceptable composition comprises a stable dispersion in an aqueous salt solution of a cationic copolymer comprising from about 5 to about 95 mole percent acrylamide and from about 5 to about 95 mole percent dimethylaminoethyl acrylate benzyl chloride quaternary salt, wherein the dispersion has an RSV from about 0.4 to about 30 dL/g.

In another preferred aspect, the cosmetically acceptable composition comprises a stable dispersion in an aqueous salt solution of a cationic copolymer comprising from about 5 to about 95 mole percent acrylamide and from about 5 to about 95 mole percent dimethylaminoethyl acrylate methyl chloride quaternary salt, wherein the dispersion has a RSV from about 0.4 to about 30 dL/g.

In another preferred aspect, the cosmetically acceptable composition comprises a stable dispersion in an aqueous salt solution of an anionic copolymer comprising from about 5 to about 95 mole percent acrylamide and from about 5 to about 95 mole percent (meth)acrylic acid or a salt thereof, wherein the dispersion has a RSV from about 0.4 to about 40 dL/g.

In another preferred aspect, the cosmetically acceptable composition comprises a stable dispersion in an aqueous salt solution of a nonionic copolymer comprising from about 5 to about 95 mole percent acrylamide and from about 5 to about 95 mole percent vinyl acetate, wherein the dispersion has a RSV from about 0.4 to about 40 dL/g.

In another preferred aspect, the cosmetically acceptable composition comprises a stable dispersion in an aqueous salt solution of a cationic polymer comprising from about 20 to about 90 mole percent acrylamide and from about 80 to about 10 mole percent of one or more cationic monomers selected from the group consisting of diallyldimethylammonium chloride, dimethylaminoethyl acrylate methyl chloride quaternary salt and dimethylaminoethyl acrylate benzyl chloride quaternary salt, wherein the dispersion has a RSV from about 0.4 to about 30 dL/g.

In another preferred aspect, the cosmetically acceptable composition is selected from the group consisting of shampoos, aftershaves, sunscreens, hand lotions, skin creams, liquid soaps, bar soaps, bath oil bars, shaving creams, dishwashing liquids, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

In another preferred aspect, the cosmetically acceptable composition further comprises one or more excipients selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylens, carageenans, gum arabic, carboxymethyl guar gum, carboxymethyl (hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid ([poly-N acetyl-neuraminic acid]), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomainans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer *Encyclopedia of Chemical Technology,* Fourth Edition, Vol. 16, John Wiley and Sons, NY pp. 578–611 (1994) which is incorporated entirely by reference. Complex carbohydrates found in Kirk-Othmer *Encyclopedia of Chemical Technology,* Fourth Edition, Vol. 4, John Wiley and Sons, NY pp. 930–948, 1995 which is herein incorporated by reference.

The cosmetically acceptable composition of this invention may include surface-active agents. Surface active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents, and dispersion polymers.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, trlethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, trlethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL™ as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Quaternary ammonium compounds can also be used in the cosmetically acceptable composition of this invention as long as they are compatible in the compositions of the invention, wherein the structure is provided in the CTFA Cosmetic Ingredient Handbook, Fifth Edition, 1988, page 40. Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof.

Examples of quaternary ammonium compounds include but are not limited to: Behentrimonium chloride, Cocotrimonium chloride, Cethethyldimonium bromide, Dibehenyldimonium chloride, Dihydrogenated tallow benzylmonium chloride, disoyadimonium chloride, Ditallowdimonium chloride, Hydroxycetyl hydroxyethyl dimonium chloride, Hydroxyethyl Behenamidopropyl dimonium chloride, Hydroxyethyl Cetyldimonium chloride, Hydroxyethyl tallowdimonium chloride, myristalkonium chloride, PEG-2 Oleamonium chloride, PEG-5 Stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41–42, incorporated herein by reference.

The cosmetically acceptable compositions may include di-long chain amines from about $C_{10}$ to $C_{22}$, long chain fatty amines from about $C_{10}$ to $C_{22}$, and mixtures thereof. Specific examples include dipalmitylamine, lauramidopropyldimethyl, stearamidopropyl dimethylamine. The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included. When used, the fatty alcohol component is included in the formulations at a concentration of about 1 to about 10 weight percent, more preferably about 2 to about 7 weight percent.

Nonionic surface-active agents, which can be used in the cosmetically acceptable composition of this invention include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, sythetic beeswax and the like may be blended together. Alkylmethyl siloxanes with varying degrees of substitution can be used to increase water retained by the skin. Siloxanes such as stearyl dimethicone, known as 2503 Wax, C30–45 alkyl methicone, known as AMS-C30 wax, and stearoxytrimethylsilane (and) stearyl alcohol, known as 580 Wax, each available from Dow Coming®, Midland, Mich., USA. Additonal alkyl and phenyl silicones may be employed to enhance moisturizing properties. Resins such as dimethicone (and) trimethylsoiloxysilicate, known as Dow Coming® 593 or Cyclomethicone (and) Trimethylsiloxysilicate, known as Dow Corning® 749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component at a temperature of 25° C. is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane, available under the tradename Dow Coming® 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., USA under the tradenames Dow Coming® 244 fluid, Dow Coming® 245 fluid, Dow Coming® 246, Dow Coming® 344 fluid and Dow Coming® 345 fluid, and Silicone SF-1173 and Silicone SF-1202 from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols, Dow Coming® 3225C and 5225C Formulation Aids, available from Dow Coming, Midland, Mich., USA and Silicone SF-1528, available from General Electric, Waterford, N.Y., USA. The side chains may also include alkyl groups such as lauryl or cetyl. Preferred are lauryl methicone copolyol, known as Dow Corning® 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, GER. When used, the silicone surfactants are preferably included in the formulations of this invention at a concentration of 0.1 to 30 weight percent, more preferably 1 to 15 weight percent.

Amine functional silicones and emulsions may be utilized in the present invention. Preferred examples include Dow Coming® 8220, Dow Coming® 939, Dow Coming® 949, Dow Coming® 2-8194, all available from Dow Coming, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises from about $C_6$ to $C_{22}$ atoms. A preferred volatile hydrocarbon is an aliphatic hydrocarbon having a chain length from about $C_6$ to $C_{16}$ carbon atoms. An example of such compound includes isohexadecane, under the tradename Permethyl 101A, available from Presperse, South Plainfield, N.J., USA. Another example of a preferred volatile hydrocarbon is $C_{12}$ to $C_{14}$ isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17$^{th}$ Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers which can be used in this invention include, but are not limited to high molecular weight crosslinked homopolymers of acrylic acid, and Acrylates/C10–30 Alkyl Acrylate Crosspolymer, such as the Carbopol® and Pemulen® series, both available from B. F. Goodrich, Akron, Ohio, USA; anionic acrylate polymers such as Salcare® AST and cationic acrylate polymers such as Salcare® SC96, available from Ciba Specialties, High Point, N.C., USA; Acrylamidopropylttrimonium chloride/acrylamide; Hydroxyethyl methacrylates polymers, Steareth-10 Allyl Ether/Acrylate Copolymer; Acrylates/Beheneth-25 Metacrylate Copolymer, known as Aculyn® 28, available from International Specialties, Wayne, N.J., USA; Glyceryl Polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The anti oxidants will be present at from 0.01 to 5 weight percent, preferably 0.1 to 3 weight percent and most preferably from 0.2 to 2 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis (hydroxypropyl) aminobenzoate, 2-ethylhexy 1-2-cyano-3, 3-diphenylacrylate, homomenthyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Example of preservatives, which may be used include, but are not limited to 1,2-dibromo-2, 4-dicyano butane (Methyldibromo Glutaronitrile, known as MERGUARD®, ONDEO Nalco Chemical Company, Naperville, Ill., USA), benzyl alcohol, imidazolidinyl urea, 1,3-bis (hydroxymethyl)-5, 5-dimethyl-2, 3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient by normally used in cosmetics. Examples of such ingredients include, but are not limited to buffering agents, fragrance ingredients, chelating agents, color additives or dyestuffs which can serve to color the composition itself or keratin, sequestering agents, softeners, foam synergistic agents, foam stabilizers, sun filters and peptizing agents.

The surface of pigments, such titanium dioxide, zinc oxide, talc, calcium carbonate or kaolin, can be treated with the unsaturated quaternary ammonium compounds described herein and then used in the cosmetically acceptable composition of this invention. The treated pigments are then more effective as sunscreen actives and for use in color cosmetics such as make up and mascara.

The cosmetically acceptable composition of this invention can be presented in various forms. Examples of such forms include, but are not limited a solution, liquid, cream, emulsion, dispersion, gel, thickening lotion.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin include leave-on or rinse-off skin care products such as lotions, hand/body creams, shaving gels or shaving creams, body washes, sunscreens, liquid soaps, deodorants, antiperspirants, suntan lotions, after sun gels, bubble baths, hand or mechanical dishwashing compositions, and the like. In addition to the polymer, skin care compositions may include components conventionally used in skin care formulations. Such components include for example; (a) humectants, (b) petrolatum or mineral oil, (c) fatty alcohols, (d) fatty ester emollients, (e) silicone oils or fluids, and (f) preservatives. These components must in general be safe for application to the human skin and must be compatible with the other components of the formulation. Selection of these components is generally within the skill of the art. The skin care compositions may also contain other conventional additives employed in cosmetic skin care formulations. Such additives include aesthetic enhancers, fragrance oils, dyes and medicaments such as menthol and the like.

The skin care compositions of this invention may be prepared as either oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, the humectant, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The dispersion polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the dispersion polymer, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples nclude the Polyquaterniums (example Polyquaternium-1 to Polyquaternium-50), Guar Hydroxypropyl Trimonium Chloride, Starch Hydroxypropyl Trimonium Chloride and Polymethacrylamidopropyl Trimonium Chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, acrylic acid thickeners available from B.F. Goodrich; xanthan gums; sodium alginates; gum arabic; cellulose derivatives and poly(ethylene oxide) based thickeners, and it is also possible to achieve thickening by means of a mixture of polyethylene glycol stearate or distearate or by means of a mixture of a phosphoric acid ester and an amide. The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given dispersion polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/

MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

If the compositions of the instant invention are intended for use in the dyeing of keratin fibers, and in particular human hair, they generally contain at least one oxidation dyestuff precursor and/or one direct dyestuff, in addition to the unsaturated quaternary ammonium compounds. They also can contain any other adjuvant normally used in this type of composition.

The pH of the dyeing compositions is generally 7 to 11 and can be adjusted to the desired value by adding an alkalizing agent.

The compositions according to this invention also can be used for waving or straightening the hair. In this case, the composition generally contains, in addition to these unsaturated quaternary ammonium compounds, one or more reducing agents and, if appropriate, other adjuvants normally used in this type of composition; such compositions are intended for use conjointly with a neutralizing composition.

The foregoing may be better understood by reference to the following Examples, which are presented for purposes of illustration and are not intended to limit the scope of this invention.

EXAMPLE 1

Film Formation and Hold Angle

The film formation and hold angle attributes are measured for representative compositions of this invention using the following protocol. The results are summnarized in Table 2.

1. Dispersion polymers of the present invention are added into deionized water and mixed for one hour or until completely dissolved.
2. Tresses are submersed in 100 ml deionized water for five seconds, ensuring that tresses are completely wetted.
3. Using gloved hands, fingers are utilized to squeeze remaining water from tress.
4. Hair tresses are next blotted one time on a paper towel until damp.
5. About 0.5 gram of test material is applied across the top of each tress.
6. While holding tress vertically, each tress is stroked 20 times in a downward fashion to ensure even coverage of material on the hair.
7. A Sally 220010 small-tooth comb is utilized to further distribute material onto the hair, replacing excess material back onto the tress to even coating. The comb separated the strands slightly.
8. The hair tresses are dried using hair dryer on low approximately 2 inches away from the tress and drying in an up and down motion at approximately 100° C. for 15 minutes on each side of tress.
9. Stiffness and film formation of each tress is evaluated by tactile means. Samples are rated on a continuous scale from 1 to 5 (1=low film formation/stiffness to 5=high film formation/high stiffness). Samples are run in triplicate.
10. Tresses are held at a horizontal position and the angle of hold is checked. The stiffness intensity is ranked from 1=least hold to 4=most hold. Higher rank indicates better hold angle.

TABLE 2

Film Rating and Hold Angle for Compositions containing Representative Dispersion Polymers

| Com-position | Composition (mole percent, percent polymer solids, RSV in dL/g) | Film Rating (average n = 3 tresses) | Hold Angle Rank (average n = 3 tresses) |
|---|---|---|---|
| A | Deionized Water Control | 1.0 | 1 |
| B | 90:10 AcAm/BCQ, 0.5%, 19.3 (15% concentration) | 3.7 | 4 |
| C | 90:10 AcAm/MCQ, 0.5%, 16 (15% concentration) | 3.3 | 3 |
| D | 70:30 AcAm/DADMAC, 0.5%, 5.3, (21% concentration) | 2.8 | 2 |

As shown in Table 2, the dispersion polymers of Example B, C, and D offer excellent film and hold angle when compared to the water control of Example A.

EXAMPLE 2

Curl Retention

The curl retention is measured for representative compositions of this invention using the following protocol. Higher percent curl retention indicates better performance. The results are summarized in Table 3.

1. Prepare 5 replicates for each polymer to be tested and three samples for the control.
2. Apply 0.5 g of 0.5% actives polymer onto tress. Stroke 25 times to ensure coverage.
3. Comb each tress five times with the wide end of the Sally styling comb to detangle.
4. Clip the hair onto a clamp that is mounted on the hair-combing stand.

5. Set the end of hair on the middle of a roller (1.7 cm in diameter) and roll the hair up so it ends up on the middle of the roller.
6. After completion of rolling, the entire set of tresses is placed under 100° C. blow dryer on low for 15 minutes on each side.
7. Humidity is adjusted between 85 and 90 percent by placing 500 grams of deionized water/170 g sodium sulfite in each of two glass baking dishes in the humidity chamber. The chamber is equilibrated.
8. The rollers are removed from the hair tresses, one by one. The curls are unwound in a helical configuration.
9. The initial lengths of all the tresses at t=0 (Initial Length= Lo) are recorded.
10. The rack of curls is placed in the humidity chamber and the timer is set for 15 minutes.
11. length (Lt) of each tress (from the bottom of the clamp to the bottom of the curl) is measured every 15 minutes for 2 hours). Note: Subsequent timings are started every time measurement of the first tress is made.
12. Curl retention is calculated using the following formula:

% Curl Retention=(L−Lt)/(L−Lo)×100

Where L=length of tress, Lt=Length of tress at time t, Lo=length of tress at time t=0.

TABLE 3

Percent Curl Retention for Compositions containing Representative Dispersion Polymers

| Time | Treatment Composition B[1] (90 mole % AcAm/10 mole % BCQ 15%, RSV 19.3) | Composition A (Water) | Composition C[1] (90 mole % AcAm/10 mole % MCQ 20%, RSV 16) | Composition D[1] (70 mole % AcAm/30 mole % DADMAC 21%, RSV 5.3) |
|---|---|---|---|---|
| 0 | 95.7 | 64 | 92.2 | 91.5 |
| 15 | 93.3 | 45 | 86.5 | 88.7 |
| 30 | 91 | 40 | 84.7 | 87.4 |
| 45 | 90 | 36 | 81.8 | 84.3 |
| 60 | 88.7 | 32.1 | 80.4 | 79.3 |
| 75 | 87.1 | 29.7 | 76.9 | 79.6 |
| 90 | 86.7 | 29.7 | 76 | 77.3 |
| 120 | 85.2 | 29.7 | 74.1 | 75.1 |

[1]Polymer compositions B, C and D are diluted to 0.5% polymer solids for the data summarized in Table 3.

As shown in Table 3, the curl retention of the polymers of Compositions B, C and D is superior to the water control of Example A.

EXAMPLE 3

Anionic Surfactant Shampoo Composition

Anionic surfactant shampoo compositions containing representative dispersion polymers are prepared as follows.

A portion of deionized water is added to beaker and heated to approximately 70° C. Disodium Laureth-3 Sulfosuccinate, Ammonium Lauryl Sulfate and Coco-glucoside are added and mixed. The PEG-120 Methyl Glucose Dioleate is melted separately and added to the batch. The parabens and coco-betaine are mixed and heated to 70° C. until dissolved and added to the batch. Fragrance is combined with Polysorbate-20 and added at a temperature less than 30° C. The pH of the shampoo is adjusted to pH 6.0 if necessary with citric acid. A separate vessel containing diluted dispersion polymer and deionized water is added to the batch and mixed until uniform. The shampoo compositions are characterized in Table 4.

TABLE 4

Anionic Surfactant Shampoo Compositions containing Representative Dispersion Polymers

| Composition (mole percent, percent polymer solids, RSV in dL/g) | F Weight % | G Weight % | H Weight % | I Weight % | J Weight % | K Weight % |
|---|---|---|---|---|---|---|
| Water, Deionized | QS | QS | QS | QS | QS | QS |
| Dispersion Polymer 90 mole % AcAm/10 mole % BCQ, 15%, RSV 19.3 | 0.00 | 1.50 | 2.50 | 0.00 | 0.00 | 0.00 |
| Dispersion Polymer 30 mole % AA/70 mole % AcAm, 25%, RSV 30 | 0.00 | 0.00 | 0.00 | 0.92 | 1.52 | 0.00 |
| Dispersion Polymer 20 mole % AcAm/50 mole % BCQ/30 mole % MCQ 21%, RSV 17.9 | 0.00 | 0.00 | 0.00 | 0.00 | 0.00 | 1.00 |
| Disodium Laureth-3 Sulfosuccinate[1] | 3.00 | 3.00 | 3.00 | 3.00 | 3.00 | 3.00 |
| Ammonium Lauryl Sulfate[2], 30% | 30.00 | 30.00 | 30.00 | 30.00 | 30.00 | 30.00 |
| Coco-glucoside[3] | 3.00 | 3.00 | 3.00 | 3.00 | 3.00 | 3.00 |
| PEG-120 Methyl Glucose Dioleate[4] | 2.10 | 2.10 | 2.10 | 2.10 | 2.10 | 2.10 |
| Coco Betaine[5] | 8.00 | 8.00 | 8.00 | 8.00 | 8.00 | 7.50 |
| Methyl Paraben[6] | 0.20 | 0.20 | 0.20 | 0.20 | 0.20 | 0.20 |
| Propyl Paraben[7] | 0.10 | 0.10 | 0.10 | 0.10 | 0.10 | 0.10 |
| Polysorbate 20[8] | 2.00 | 2.00 | 2.00 | 0.00 | 0.00 | 0.00 |
| Fragrance | 0.10 | 0.10 | 0.10 | 0.00 | 0.00 | 0.00 |

TABLE 4-continued

Anionic Surfactant Shampoo Compositions containing Representative Dispersion Polymers

| Composition (mole percent, percent polymer solids, RSV in dL/g) | F Weight % | G Weight % | H Weight % | I Weight % | J Weight % | K Weight % |
|---|---|---|---|---|---|---|
| Fragrance | 0.086 | 0.086 | 0.086 | 0.00 | 0.00 | 0.00 |
| Citric Acid, 50%[9] | QS | 0.15 | 0.15 | 0.15 | 0.15 | 0.15 |
| Visual Observation | clear | hazy | hazy | hazy | hazy | Slight haze |

[1]Geropon SBFA-30, Rhone-Poulenc, Cranbury, NJ, USA.
[2]Standapol A, Cognis Corporation, Hobokin, NJ, USA.
[3]Plantaren 818UP, Cognis Corporation, Hobokin, NJ, USA.
[4]Glucamate ® DOE-120, Amerchol Corporation, Edison, NJ, USA.
[5]Velvetex AB45, Cognis Corporation, Hobokin, NJ, USA.
[6]Nipagin ®, NIPA Inc., Wilmington, DE, USA.
[7]Nipasol ®, NIPA Inc., Wilmington, DE, USA.
[8]Tween ® 20, Uniqema, Wilmington, DE, USA.
[9]EM Science, Gibbstown, NJ, USA.

EXAMPLE 4
Shampoo Viscosity

The viscosity of the shampoo compositions prepared in Example 3 are measured on a Brookfield RV-DV I+using spindle 3 at speed 20 for 60 seconds. The results are summarized in Table 5.

TABLE 5

Shampoo Viscosity without and with Dispersion Polymers

| Composition | Dispersion Polymer (mole percent, percent polymer solids, RSV in dL/g) | Viscosity (cps) |
|---|---|---|
| F (no polymer) | No polymer | 4950 |
| G (0.23% active) | 90:10 AcAm/BCQ/, 25, 19.3 | 3730 |
| H (0.38% active) | 90:10 AcAm/BCQ, 25, 19.3 | 3500 |
| I 0.92% (0.23% active) | 30:70 AA/AcAm, 25, 30 | 4310 |
| J 1.52% (0.38% active) | 30:70 AA/AcAm, 25, 30 | 4170 |
| K (0.2% active) | 20:50:30 AcAm/BCQ/MCQ, 21, 16 | 4410 |

As shown in Table 5, shampoos can be formulated with dispersion polymers at acceptable viscosities of at least 3000 centipoise.

EXAMPLE 5
Lather Potential

Since the ability of shampoos to form a dense lather is of primary importance for product performance, an empirical test to estimate the lathering properties of several shampoo formulations with and without dispersion polymer is performed. The test protocol is as follows. This test is a slight modification of the Hart DeGeorge Test.
1. 200 mL of test solution (18% by weight) is added to a Waring blender, covered tightly and run on high speed for sixty seconds.
2. After the blender stopped, the foamed solution is immediately poured into funnel resting over a mesh sieve. A stopwatch is started immediately at the beginning of the pour. The cup is held inverted over the funnel (at 60 degrees) for 15 seconds and then removed.
3. The foam is observed carefully. As soon as any metal from the wire in the funnel is clearly seen, the drain time is recorded in seconds.
4. The equipment is rinsed with tap and deionized water and allowed to drain for sixty seconds.
5. The test is repeated three times and the results are averaged.
6. The drainage times are reported in seconds.

TABLE 6

Hart DeGeorge Lather Test and Creaminess Panel

| Composition | Drainage Time (s) | Foam Creaminess |
|---|---|---|
| F (Control shampoo) | 52 | Control |
| K (Dispersion Polymer Shampoo) | 54 | Richer, denser |

As shown in Table 6, the foam drain time is not affected by polymer but foam is perceived by three panelists to be creamier (richer, denser) versus control without dispersion polymer.

EXAMPLE 6
Water-in-Silicone Oil Emulsion

The water-in-silicone emulsion containing a representative dispersion polymer shown in Table 7 is prepared by separately mixing an oil phase and water phase containing salt and dispersion polymer. The water phase is then added to the oil phase over 30 minutes with vigorous agitation using a high turbulence mechanical blade mixer set at high speed (900 ft/min.).

TABLE 7

Water-in-Silicone Oil Emulsion containing a Representative Dispersion Polymer

|  | Composition L |
|---|---|
| Dimethicone Copolyol[1], 10% | 10.20 |
| Decamethyl trisiloxane[2] or dimethicone 10 centistoke fluid | 10.00 |
| Cyclopentasiloxane[3] | 20.00 |
| 90 mole % AcAm/10 mole % BCQ, 20%, RSV 19.3 | 2.00 |
| Ammonium Sulfate[4] | 1.00 |
| Deionized Water | 56.80 |

[1]Dow Corning ® Formulation Aid 5225C, Dow Corning, Midland, MI, USA.
[2]Dow Corning ® 200 10 Centistoke fluid, Dow Corning, Midland, MI, USA.
[3]Dow Corning ® 245 fluid, Dow Corning, Midland, MI, USA.
[4]Ammonium sulfate is obtained from EM Science, Gibbstown, NJ, USA.

EXAMPLE 7
Wet Combing Assessment

The wet combability of hair treated with the water-in-silicone oil emulsion of Example 6 is assessed as described below. The results are summarized in Table 8.

1. 1-g samples, six inches in length each of virgin hair from International Hair Importers are prepared.
2. 1 g of dispersion polymer is applied onto tress. Each tress is stroked 25 times to ensure coverage.
3. Each tress is combed with the wide end of the Sally styling comb to detangle.
4. Each tress is rinsed under 43° C. water for thirty seconds.
5. Excess water is removed with fingers.
6. A panel is randomized.
7. Panelists comb and rate tresses according to intensity (1=no drag, easy to comb to 5=drag and pull, very hard to comb).

TABLE 8

Wet Combing of Water-in-Silicone Oil Emulsion containing a Representative Dispersion Polymer

| Composition | Rating (n = 4 panelists) |
|---|---|
| Control | 2.69 |
| L | 1.83 |

As shown in Table 8, Composition L (Example 6) deep-conditioned the hair and is more easily combed versus untreated hair.

EXAMPLE 8
Application of Water-In-Silicone Oil Emulsion to Skin

One g of the water-in-silicone oil emulsion of Example 7 is applied and worked into the skin. The skin lotion provided silky and slippery feel and water repellency when skin is wetted with water.

EXAMPLE 9
Hair Coloring Compositions containing Representative Dispersion Polymers Several auburn commercial hair colors are utilized to investigate the performance of dispersion polymers in oxidative color systems. Compositions M and N are permanent hair colors with a representative dispersion polymer in the peroxide portion of the two-part system.

Color System 1: Part 1 contains water, MEA-Oleate, isopropyl alcohol, ethanolamine, PEG-2 cocamine, Lauramide MEA, sodium laureth sulfate, potassium cocoyl hydrolyzed collagen, wheat amino acids, Hypnea Musciformis extract, Gellidiela Acerosa extract, Sargasum Filipendula extract, sorbitol, Meadowfoam seed oil, oleyl alcohol, Polyquaternium-28, Laneth-5, sodium benzotriazolyl butylphenol sulfonate, buteth-3, tributyl citrate, sodium sulfite, erythorbic acid, tetrasodium EDTA, fragrance, p-phenylinediamine, 2-methyl resorcinol, p-aminophenol, resorcinol, phenyl methyl pyrazolone, 4-amino-2-hydroxy toluene.

Part 2 contains water, hydrogen peroxide, and phosphoric acid with or without 0.5% polymer solids 90% AcAm/10 mole % DMAEA•BCQ (Composition M).

A second hair dye system is also examined. Part 1 contains: water, Trideceth-2 Carbozamide MEA, butoxydiglycol, propylene glycol, PEG-2 tallow amine, denatured alcohol, oleyl alcohol, polyglyceryl-2 oleyl ether, ammonium hydroxide, oleic acid, sodium diethylaminopropyl cocoaspartamide, 4-amino-2-hydroxytoluene, pentasodium pentetate, fragrance, ammonium acetate, sodium metabisulfite, erythorbic acid, p-phenylene diamine, p-aminophenol, 2-methyl-5-hydroxyethylaminophenol, phenyl methyl pyrazole, resorcinol 6 and hydroxyindole.

Part Two contains water, hydrogen peroxide and phosphoric acid with or without 0.5% polymer solids 90% AcAm/10% DMAEA•BCQ (Composition N).

An equal amount of parts 1 and 2 are mixed and 1 g of dye is applied to approximately 2 g bleached hair tresses and brushed through with a color brush. Processing is allowed to proceed at room temperature (23° C.) for thirty minutes. Each tress is then rinsed in 43° C. tap water to remove the dye.

In each case, the application slip of the product with dispersion polymer is enhanced, and the brushing and spreading of the dye onto the hair is made easier. Rinsing aesthetics are also more slippery. Triplicate tresses treated with the hair dye containing dispersion polymers (Compositions M and N) did not negatively affect the deposition of the auburn color or affect the particular color obtained.

EXAMPLE 10
Silicone Shampoos containing Representative Dispersion Polymers

The ability of shampoos to form a dense lather is associated with the tactile properties of lubricity and slip. Several silicone shampoos are formulated with representative dispersion polymers of this invention.

Composition O is a commercial shampoo containing: water, sodium laureth sulfate, cocamidoproyl betaine, dimethiconol, silk protein, sodium chloride, fragrance, propylene glycol, carbomer, Mica, PPG-9, guar hydroxypropyltrimonium chloride, tetrasodium EDTA, DMDM hydantoin, TEA-dodecylbenzensulfonate, methenamine, methylchloroisothiazolinone, methylisothiazolinone and titanium dioxide with various amounts of dispersion polymer. The slippery feel of Composition O is improved by addition of 0.1 weight % of an anionic dispersion polymer (30 mole % Acrylic Acid/70 mole % Acylamide, 25%, RSV 30) of the present invention.

Preparation of Compositions P and Q

The polyquaternium-47 solution and part of the water is mixed. In a separate beaker, the silicone and Ammonium Lauryl Sulfate are combined and homogenized until uniform. The polyquaternium-47 solution is added to the silicone/surfactant mixture and is heated to 65° C. The Stearic acid, Disodium EDTA, Cocamide MEA and Ethylene Glycol Distearate are added in order and mixed. The surfactant base is cooled and the pH adjusted to about pH 6.5. Methyl dibromo Glutaronitrile (and) phenoxyethanol are added after the batch is at a temperature of 30° C. For Example Q, a solution of dispersion polymer is added to the base.

Preparation of Compositions R, S and T

The dispersion polymer of the present invention and part of the water is mixed. In a separate beaker, Deionized water and Ammonium Lauryl Sulfate are combined until uniform. Upon heating to 90° C., Cocamide MEA is added to the batch and mixed. Temperature is maintained for thirty minutes. The surfactant base is cooled and the pH adjusted to about pH 6.5. Methyl dibromo Glutaronitrile (and) phenoxyethanol and Disodium EDTA are added at 30° C. The dimethicone emulsion is added and mixed. For Compositions S and T, a solution of dispersion polymer is added to the base.

The shampoo compositions are shown in Table 9. In Table 9, compositions Q, S, and T are representative dispersion polymer-containing compositions of this invention. Compositions P and R are control silicone shampoos without polymer.

The Shampoo compositions containing dispersion polymer give a very slippery and creamy feel upon application.

TABLE 9

Silicone Shampoo Compositions

| Composition (mole percent, percent polymer solids, RSV in dL/g) | P Weight % | Q Weight % | R Weight % | S Weight % | T Weight % |
|---|---|---|---|---|---|
| Water, Deionized | QS to 100 | QS to 100 | QS to 100 | QS to 100 | QS to 100 |
| Polyquaternium-47[1] | 1.00 | 1.00 | 0 | 0 | 0 |
| 30% mol AA/70% mol AcAm, 25%, RSV 30 | 0 | 0.75 | 0 | 0.75 | 0 |
| 65% mol AcAm/25% mol BCQ/10% mol MCQ, 20%, RSV 20.8 | 0 | 0 | 0 | 0 | 0.935 |
| 20% mol AcAm/50% mol BCQ/30% mol MCQ, 25%, RSV 16 | 0 | 0 | 0 | 0 | 0.20 |
| Polydimethylsiloxane, 350 CST[2] | 1.00 | 1.00 | 0 | 0 | 0 |
| Dimethiconol and TEA-Dodecylbenzenesulfonate[3] | 0 | 0 | 1.00 | 1.00 | 1.00 |
| Ammonium Lauryl Sulfate[4] | 46.00 | 46.00 | 46.00 | 46.00 | 46.00 |
| Stearic Acid[5] | 1.30 | 1.30 | 0 | 0 | 0 |
| Disodium EDTA[6] | 0.15 | 0.15 | 0.10 | 0.10 | 0.10 |
| Cocamide MEA[7] | 1.30 | 1.30 | 3.00 | 3.00 | 3.00 |
| Ethylene Glycol Distearate[8] | 1.00 | 1.00 | 0 | 0 | 0 |
| Methyldibromo Glutaronitrile in phenoxyethanol, 20%[9] | 0.15 | 0.15 | 0 | 0 | 0 |
| DMDM Hydantoin[10] | 0 | 0 | 0.25 | 0.25 | 0.25 |
| Ammonium Hydroxide, 28% | Qs to pH 6.5 | Qs to pH 6.5 | 0 | 0 | 0 |
| Sodium Hydroxide, 50% | 0 | 0 | Qs to pH 7.0 | Qs to pH 7.0 | Qs to pH 7.0 |
| Ammonium Chloride | Qs | Qs | 0 | 0 | 0 |
| Sodium Chloride | 0 | 0 | 0 | 0 | 0 |

[1]ONDEO Nalco, Naperville, IL, USA.
[2]Dow Corning 200 ® Fluid, 350 CST, Dow Corning, Midland, MI, USA.
[3]Dow Corning ®1784, Dow Corning, Midland, MI, USA.
[4]Standapol A, Cognis Corporation, Hobokin, NJ, USA.
[5]Emersol 132, Henkel Corporation, city, state.
[6]Versene ®, Dow Chemical, Midland, MI, USA.
[7]Ninol ® CMP, Stepan Company, Northfield, IL, USA.
[8]Tegin ® EGS, Goldschmidt, Hopewell, VA, USA.
[9]Merguard ® 1200, ONDEO Nalco, Naperville, IL, USA.
[10]Glydant ®, Lonza, Fairlawn, NJ, USA.

EXAMPLE 11
Lubricity and Creaminess of Lather Test

A sensory panel performed lubricity and creaminess of lather tests as follows. One g of shampoo is placed onto 2 g bleached tresses and washed for 30 seconds followed by a 10 second rinse under 43° C. tap water. Panelist findings indicate richer and creamier lather when dispersion polymer is included in the formulations.

TABLE 10

Lubricity and Creaminess of Lather Test

| Shampoo | Lubricity | Creaminess of Lather |
|---|---|---|
| Composition O (Commercial shampoo with dispersion polymer) | Enhanced | Enhanced |
| Example P - control | Very good | Very good |
| Example Q | Very good Enhanced slip | Very good Enhanced, richer |
| Example R - control | Very good | Very good |
| Example | Enhanced slip | Enhanced, richer |
| Example T | Enhanced slip | Enhanced, richer |

As can be seen from the qualitative panelist results summarized in Table 10, dispersion polymers enhance the performance of the silicone-containing shampoo even when other polymers such as polyquaternium-47 (Composition Q) or guar (Composition O) are present.

EXAMPLE 12
Leave-on or Rinse-off Conditioner or Styling Créme

Leave-in or rinse off conditioner and styling créme compositions containing representative dispersion polymers are shown in Table 11. The compositions are prepared by adding thickener to deionized water and mixing. Some of the water is mixed with the dispersion polymers of the present invention and added into the batch. Volatile silicone is added. Polyvinyl pyrrolidone is added to Example W.

TABLE 11

Leave-in or Rinse-off Conditioner and Styling Cremes containing Representative Dispersion Polymers

| Composition | U Weight % | V Weight % | W Weight % |
|---|---|---|---|
| Water, Deionized | qs | Qs | qs |
| Sodium Acrylates Copolymer and Glycine soja and PPG-1 Trideceth-6[1], 50% | 3.50 | 0 | 0 |
| Polyquaternium-37/Propylene glycol/Dicaprylate Dicaprate and PPG-1 Trideceth-6[2], 50% | 0 | 3.00 | 3.00 |
| 30 mole % AA/70 mole % AcAm, Dispersion Polymer 25%, RSV 30 | 1.00 | 0 | 0 |
| 70 mole % AcAm/30 mole % DADMAC Dispersion Polymer, 21%, RSV 5.3 | 0 | 1.00 | 1.00 |

TABLE 11-continued

Leave-in or Rinse-off Conditioner and
Styling Cremes containing Representative Dispersion Polymers

| Composition | U Weight % | V Weight % | W Weight % |
|---|---|---|---|
| Polyvinypyrollidone[3] | 0 | 0 | 1.00 |
| Cyclopentasiloxane[4] | 2.00 | 1.50 | 1.50 |

[1]Salcare ® AST, Ciba Specialty Chemicals, Highpoint, NC, USA.
[2]Salcare ® SC96, Ciba Specialty Chemicals, Highpoint, NC, USA.
[3]PVP-K30, International Specialties Products, Wayne, NJ, USA.
[4]Dow Corning ® 245 fluid, available from Dow Corning, Midland, MI, USA.

As can be seen from Compositions U, V, and W, dispersion polymers are suitable for making conditioners and styling cremes for either leave-on or rinse-off applications. The dispersion polymers can be chosen to exhibit conditioning and moisturization or holding power depending on the dispersion polymer structure. Hair swatches are treated with 1 g of composition U, V, or W and either rinsed-off or left to remain on the hair. In all cases, compositions U, V and W each improve the wet combing of the hair tress versus the untreated slightly bleached control.

EXAMPLE 13

Conditioning Compositions

Conditioning compositions containing representative dispersion polymers are shown in Table 12. The compositions are prepared in the following manner. Hydroxyethyl cellulose and Hydroxyethylethyl cellulose are dissolved in deionized water. The pH is adjusted with citric acid. The water is heated and stearamidoproyldimethylamine is melted into the batch. Once uniform, the fatty alcohols and quaternary materials are added. A Temperature of about 80° C. is maintained for thirty minutes. Upon cooling, tetrasodium EDTA is added. Preservative and cyclopentasiloxane are then added at or below a temperature of about 40° C.

TABLE 12

Leave-in or Rinse-off Conditioner
Compositions containing Representative Dispersion Polymers

| Composition | X Weight % | Y Weight % | Z Weight % |
|---|---|---|---|
| Water, Deionized | qs | qs | qs |
| Hydroxy ethyl cellulose[1] | 0.20 | 0.20 | 0.20 |
| Hydroxyethyl ethyl cellulose[2] | 0.10 | 0.10 | 0.10 |
| Citric acid, 50%[3] | 0.171 | 0.171 | 0.171 |
| Stearamidopropyl dimethylamine[4] | 0.574 | 0.574 | 0.574 |
| Stearyl Octyldimonium methosulfate, 85%[5] | 1.493 | 1.493 | 1.493 |
| Soy alkyl trimethyl ammonium chloride, 60% in propylene glycol[6] | 0.1 | 0.1 | 0.1 |
| Cetyl alcohol[7] | 3.0 | 3.0 | 3.0 |
| Stearyl alcohol[8] | 3.0 | 3.0 | 3.0 |
| Tetrasodium EDTA[9] | 0.1 | 0.1 | 0.1 |
| Methyldibromo Glutaronitrile in Propylene Glycol, 5%[10] | 0.17 | 0.17 | 0.17 |
| 90 mole % AcAm/10 mole % BCQ, RSV 19.3 | 0 | 0.25 | 0 |
| 70 mole % AcAm/30 mole % DADMAC Dispersion Polymer, 21%, RSV 5.3 | 0 | 0 | 0.25 |
| Decamethylsiloxane[11] | 1.00 | 1.00 | 1.00 |

[1]Natrosol 250 HHR, Hercules Incorporated, Wilmington, DE, USA.
[2]Elfacos CD481, Akzo Nobel Surface Chemistry, McCook, IL, USA.
[3]Available from VWR, Westchester, PA, USA.
[4]Incromine SB, Croda, Parsippany, NJ, USA.
[5]Arquad HTL8MS, Akzo Nobel Surface Chemistry, McCook, IL, USA.
[6]Arquad SV60 PG, Akzo Nobel Surface Chemistry, McCook, IL, USA.
[7]Crodacol C-95NF, Croda, Parsippany. NJ, USA.
[8]Crodacol S-95NF, Croda, Parsippany. NJ, USA.
[9]Versene ® 100, Dow Chemical, Midland, MI, USA.
[10]Merguard ® 1200, ONDEO Nalco, Naperville, IL, USA.
[11]Dow Corning ® 200 fluid, 10 Cst, Dow Corning, Midland, MI, USA.

As can be seen from Examples Y and Z, dispersion polymers are utilized to make conditioners for either leave-on or rinse-off applications. In general, the dispersion polymers can be chosen to exhibit light or heavier conditioning and moisturization depending on the dispersion polymer structure. The fatty alcohol, quaternary and type of silicone can also be varied to provide either light or robust conditioning for different hair types.

Hair swatches are treated with 1 g of compositions X, Y and Z and either rinsed-off or left to remain on the hair. In all cases, compositions X, Y and Z each improved the lubricity upon application and improved the dry feel and body of the hair tress hair tress versus the untreated slightly bleached control. After combing the hair ten times with a plastic comb, tresses treated with conditioner had less static than the untreated bleached control.

EXAMPLE 14

Shaving Gel/Cream

Shaving products in general need to have several positive characteristics to be successful. They must be easily spread onto the skin, have a high lubricity and razor glide to reduce the possibility of nicks and cuts of the skin, have rich and creamy foam, enhance skin feel during and/or after the shaving process and inhibit drying of the skin.

Shaving gel compositions without and with representative dispersion polymer are shown in Table 13. The compositions are prepared as follows.

Deionized water and hydroxypropylmethylcellulose are mixed until uniform. The solution is pH adjusted to about 8.5 and heated to about 80° C. The oily components are added along with the Polysorbate-60. Preservatives are added at a temperature below 40° C. To compositions BB, CC, DD, EE and FF, dispersion polymers are mixed in water separately and then added to the batch at the end.

TABLE 13

Shaving Gel Compositions without and with Representative Dispersion Polymers

| Composition (mole percent, percent polymer solids, RSV in dL/g) | AA eight % | BB eight % | CC Weight % | DD Weight % | EE Weight % | FF Weight % |
|---|---|---|---|---|---|---|
| Water, Deionized | 83.23 | 82.23 | 82.23 | 82.23 | 82.23 | 82.23 |
| Hydroxyl propylmethylcellulose[1] | 4.00 | 4.00 | 4.00 | 4.00 | 4.00 | 4.00 |
| Stearic Acid[2] | 6.00 | 6.00 | 6.00 | 6.00 | 6.00 | 6.00 |
| Polysorbate-60[3] | 2.00 | 2.00 | 2.00 | 2.00 | 2.00 | 2.00 |
| Triethanolamine, 99%[4] | 2.47 | 2.47 | 2.47 | 2.47 | 2.47 | 2.47 |
| DMDM Hydantoin[5] | 0.10 | 0.10 | 0.10 | 0.10 | 0.10 | 0.10 |
| Methyldibromo Glutaronitrile in Propylene Glycol, 5%[6] | 0.20 | 0.20 | 0.20 | 0.20 | 0.20 | 0.20 |
| Glycerol[7] | 2.00 | 2.00 | 2.00 | 2.00 | 2.00 | 2.00 |
| Citric Acid, 50% | Qs | qs | qs | qs | qs | qs |
| 70 mole % AcAm/30 mole % DADMAC 21%, RSV 5.3 | 0 | 1.00 | 0 | 0 | 0 | 0 |
| 30 mole % AA/70 mole % AcAm, 25%, RSV 30 | 0 | 0 | 1.00 | 0 | 0 | 0 |
| 20 mole % AcAm/50 mole % BCQ/30 mole % MCQ, 25%, RSV 0.4 | 0 | 0 | 0 | 1.00 | 0 | 0 |
| 20 mole % AcAm/50 mole % BCQ/30 mole % MCQ, 25%, RSV 3.9 | 0 | 0 | 0 | 0 | 1.00 | 0 |
| 20 mole % AcAm/50 mole % BCQ/30 mole % MCQ, 25%, RSV 11.8 | 0 | 0 | 0 | 0 | 0 | 1.00 |

[1]Methocel ® 40-100, Dow Chemical, Midland, MI, USA.
[2]Emersol 132, Henkel Corporation, city, state.
[3]Tween ® 60, Uniqema, Wilmington, DE, USA.
[4]Triethanolamine 99, Dow Chemical, Midland, MI, USA.
[5]Glydant ®, Lonza, Fairlawn, NJ, USA.
[6]Merguard ® 1200, ONDEO Nalco, Naperville, IL, USA.
[7]EM Science, Gibbstown, NJ, USA.

Shaving gel compositions BB, CC, DD, EE and FF containing representative dispersion polymers had more lubricity than the control composition AA. Composition FF containing a polymer with an 11.8 RSV had the most slippery feel and took longer to rinse off the skin than Examples DD and EE (containing polymer with lower RSV values). However, all samples with dispersion polymer are easy to spread onto the skin, provided lubrication for the razor blade and displayed good wettability and improved quality of the lather.

EXAMPLE 15
UV Absorbance of Dispersion Polymers

The polymers of this invention can be utilized to protect against ultraviolet radiation. Any polymer containing DMAEMA-BCQ, and DMAEMA-BCQ/DMAEMA-MCQ or other monomers cited in this invention can absorb in the ultraviolet region of light from about 210 nm to about 330 nm and can be used to protect hair or skin from ultraviolet damage.

EXAMPLE 16
Hair Bodifier and Hair Straightener

The polymers of this invention can also be used to condition and help protect the hair from over processing. Hair bodifier and hair straightener compositions containing representative dispersion polymers are shown in Table 15.

Compositions GG and HH are prepared in the following manner.

Chelant is added to deionized water. Sodium and ammonium sulfate are combined and added to the chelant solution. Ammonium thiogylcolate is added and the pH adjusted to about 8.0. Separately, solutions of dispersion polymer are created with part of the water and added to batch.

TABLE 15

Hair Bodifier and Hair Straightener Compositions containing Representative Dispersion Polymers

| Composition (mole percent, percent polymer solids, RSV in dL/g) | GG Weight % | HH Weight % |
|---|---|---|
| Water, Deionized | Qs | Qs |
| Tetrasodium EDTA[1] | 0.10 | 0.10 |
| Ammonium Thioglycolate, 60%[2] | 12.4 | 12.4 |
| Ammonium Hydroxide, 28% | 4.1 | 4.1 |
| Ammonium Sulfate | 1.32 | 1.32 |
| Sodium Sulfate | 1.0 | 1.0 |
| 20 mole % AcAm/30 mole % MCQ/50 mole % BCQ, 25%, RSV 3.9 | 1.00 | 0 |
| 70 mole % AcAm/30 mole % DADMAC, 25% RSV 5.3 | 0 | 1.00 |

[1]Versene ® 100, Dow Corning, Midland, MI, USA.
[2]Hampshire/Evans, Lexington, MA, USA.

EXAMPLE 17
Hydrogen Peroxide Bodifier and Oxidizer

The dispersion polymers of this invention are also used to thicken hydrogen peroxide solutions for hair bodification via oxidation of disulfide bonds. These solutions can also be utilized in neutralizers to reform reduced cysteine bonds from perming or straightening. Hydrogen peroxide bodifier and oxidizer compositions containing representative dispersion polymers are shown in Table 16.

The compositions are prepared by dissolving dispersion polymer into water and then adding hydrogen peroxide. The pH is adjusted with phosphoric acid to stabilize the peroxide at pH 3.0.

TABLE 16

Hydrogen Peroxide Bodifier and Oxidizer Compositions containing Representative Dispersion Polymers

| Composition (mole percent, percent polymer solids, RSV in dL/g) | II Weight % | JJ Weight % |
|---|---|---|
| Water, deionized | qs | qs |
| Hydrogen Peroxide, 35% | 17.14 | 17.14 |
| Phosphoric Acid, 85% | Qs to pH 3.0 | Qs to pH 3.0 |
| 90 mole % AcAm/10 mole % BCQ, 0.5% (15%, RSV 19.3, 15%) | 1.00 | 0 |
| 70 mole % AcAm/30 mole % DADMAC 20%, RSV 5.3 | 0 | 1.00 |

EXAMPLE 18

Curl Compression

The curl compression is measured for representative compositions of this invention using the following protocol.
1. 1.5 g of polymer composition is placed onto tresses.
2. The hair is clipped onto a clamp mounted on a hair-combing stand.
3. The end of the hair is set on the middle of a roller (1.7 cm in diameter) and rolled up so it ends up on the middle of the roller.
4. After completion of rolling, the entire set of tresses is placed under a 100° C. blow dryer on low for 5 minutes.
5. The tresses are allowed to equilibrate for three hours at 50% Relative Humidity and 25° C.
6. The rollers are removed from the hair tresses, one by one. The curls are unwound in a helical configuration.

Curl compression is conducted on the DiaStron Miniature Tensile Tester (MTT170/670) to measure the stiffness of hair curls subjected to hair lacquers or setting gels. Hair curls are held between two hold-clips and the curl compression plate is designed to contact the curl as the MTT170/670 executes the method. Protocols are run to look at the curl hold over multiple cycles. The settings are:

| | |
|---|---|
| Curl Diameter (mm): | 25 |
| Curl Compression (%): | 15 |
| Hold Time (sec): | 2 |
| Rate (mm/min): | 10 |
| Maximum Force (gmf): | 300 |
| Gauge Force (gmf): | 1 |

Representative polymer compositions are shown in Table 17. The results are summarized in Table 18.

TABLE 17

Composition (mole percent, percent polymer solids, RSV in dL/g)

| | | |
|---|---|---|
| KK | 20:50:30 AcAm/BCQ/MCQ, 25, 3.9 | 4.00% and pH 6.0 (1.0% active) |
| LL | 20:50:30 AcAm/BCQ/MCQ, 25, 0.4 | 4.00% and pH 6.0 (1.0% active) |
| MM | 20:50:30 AcAm/BCQ/MCQ, 25, 11.9 | 4.00% and pH 6.0 (1.0% active) |
| NN | 30:70 AA/AcAm, 25, 30 | 4.00% and pH 6.0 (1.0% active) |
| OO | 70:30 AcAm/DADMAC, 20, 5.3 | 5.00% and pH 6.0 (1.0% active) |

TABLE 18

Curl Compression of Representative Dispersion Polymers

| Study No:1(x) | Composition KK(gmf) | Composition LL(gmf) | Composition MM(gmf) | Composition NN(gmf) | Composition OO(gmf) |
|---|---|---|---|---|---|
| 0 | 2.5 | | 2.25 | 3.5 | 1.7 |
| 0.11 | 3.75 | | 10.75 | 24.25 | |
| 0.198 | 5 | 1.2 | 17.5 | 38 | 15.7 |
| 0.309 | 5.75 | 1.2 | 25.5 | 50.25 | 23.2 |
| 0.397 | 6.5 | 1. | 30 | 58.75 | 2 |
| 0.507 | 7.25 | 1.7 | 34.75 | 71.5 | 35.7 |
| 0.618 | | 1.7 | 40.25 | 83.75 | 4 |
| 0.706 | 8.5 | | 44.5 | 92.5 | 46.7 |
| 0.794 | 9 | | 48.25 | 100.5 | 51. |
| 0.904 | 9.75 | 2.2 | 53 | 110.25 | 57.2 |
| 1.014 | 10.5 | 2.2 | 57.75 | 118.75 | 6 |
| 1.103 | 11 | 2. | 61.25 | 126.75 | 67.2 |
| 1.213 | 11.5 | 2. | 65.75 | 134.5 | 72.2 |
| 1.301 | 12.25 | 2.7 | 69 | 144.25 | 76. |
| 1.411 | 12.75 | 2.7 | 73.75 | 152.25 | 81. |
| 1.5 | 13.25 | 2.7 | 77.25 | 159.5 | 85. |
| 1.61 | 14 | | 81.5 | 167.5 | 9 |
| 1.698 | 14.25 | | 84 | 173.75 | 9 |
| 1.808 | 15 | 3.2 | 88 | 182.5 | 98. |
| 1.897 | 15.25 | 3.2 | 91.25 | 188.75 | 102.2 |
| 2.007 | 16 | 3. | 94.75 | 195.5 | 106.7 |
| 2.095 | 16.5 | 3. | 97.75 | 202.5 | 110.2 |
| 2.205 | 17 | 3. | 101.25 | 212.25 | 113.2 |
| 2.316 | 17.5 | 3.7 | 104.5 | 219.5 | 117.2 |
| 2.404 | 18 | 3.7 | 107.25 | 225.25 | 120. |
| 2.514 | 18.5 | | 110.5 | 231.5 | 124.7 |
| 2.602 | 18.75 | | 113.25 | 237.75 | 127.7 |
| 2.713 | 19.25 | | 116 | 244.75 | 131.7 |
| 2.801 | 19.75 | 4.2 | 118.75 | 249.25 | 135.2 |
| 2.911 | 20.25 | 4.2 | 121 | 253.25 | 139.2 |
| 3.021 | 20.75 | 4.2 | 124.25 | 259.5 | 143.2 |
| 3.11 | 21.25 | 4.2 | 126.75 | 262.5 | 146. |
| 3.198 | 21.75 | 4. | 129.25 | 268.25 | 149. |
| 3.308 | 22.25 | 4. | 131.75 | 272.75 | 153. |
| 3.396 | 22.75 | 4.7 | 133.25 | 277.75 | 157.2 |
| 3.507 | 23.25 | 4.7 | 135.75 | 285.25 | 161.2 |
| 3.595 | 23.5 | 4.7 | 137.5 | 289.25 | 16 |

As can be seen from the above data, the dispersion polymers of the present invention can be utilized as hair agents to set the hair. The RSV and chemistry can be changed to vary the compression force. Compositions MM and OO give similar results after the last compression, while Compositions KK and LL require significantly lower force for compression. Composition NN gives the highest compression force of the dispersion polymers tested.

Various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method of treating hair, skin or nails comprising applying to the hair, skin or nails a cosmetically acceptable composition comprising from about 0.001 to about 25 weight percent, based on polymer solids, of a stable dispersion in an aqueous salt solution of a cationic, anionic or nonionic polymer having a weight average molecular weight of from about 10,000 to about 50,000,000 g/mol and a reduced specific viscosity of about 0.4 to about 40 dl/g.

2. The method of claim 1 wherein the cationic, anionic or nonionic polymer has a weight average molecular weight of from about 100,000 to about 30,000,000 g/mol.

3. The method of claim 1 wherein the cosmetically acceptable composition further comprises one or more excipients selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, Catty alcohols, ethoxylated fatty alcohols and di-tail phospholipids.

4. The method of claim 1 wherein the cosmetically acceptable composition is selected from the group consisting of shampoos, aftershaves, sunscreens, band lotions, skin creams, liquid soaps, bar soaps, bath oil bars, shaving creams, dishwashing liquids, conditioners, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

5. The method of claim 4 wherein the cosmetically acceptable composition comprises from about 0.01 to about 5 weight percent, based on polymer solids, of the cationic, anionic or nonionic polymer.

6. The method of claim 1 wherein the cosmetically acceptable composition comprises a stable dispersion in an aqueous salt solution of a cationic copolymer comprising from about 5 to about 95 mole percent diallyldimethylammonium chloride and from about 95 to about 5 mole percent acrylamide, wherein the dispersion has a reduced specific viscosity from about 0.4 to about 12 dL/g.

7. The method of claim 1 wherein the cosmetically acceptable composition comprises a stable dispersion in an aqueous salt solution of a cationic terpolymer comprising from about 5 to about 90 mole percent acrylamide, from about 5 to about 90 mole percent dimethylaminoethyl acrylate benzyl chloride quaternary salt and from about 5 to about 90 mole percent dimethylaminoethyl acrylate methyl chloride quaternary salt wherein the dispersion has a reduced specific viscosity from about 0.4 to about 30 dL/g.

8. The method of claim 1 wherein the cosmetically acceptable composition comprises a stable dispersion in an aqueous salt solution of a cationic copolymer comprising from about 5 to about 95 mole percent acrylamide and from about 5 to about 95 mole percent dimethylaminoethyl acrylate benzyl chloride quaternary salt wherein the dispersion has a reduced specific viscosity from about 0.4 to about 30 dL/g.

9. The method of claim 1 wherein the cosmetically acceptable composition comprises a stable dispersion in an aqueous salt solution of a cationic copolymer comprising from about 5 to about 95 mole percent acrylamide and from about 5 to about 95 mole percent dimethylaminoethyl acrylate methyl chloride quaternary salt, wherein the dispersion has a reduced specific viscosity from about 0.4 to about 30 dL/g.

10. The method of claim 1 wherein the cosmetically acceptable composition comprises a stable dispersion in an aqueous salt solution of an anionic copolymer comprising from about 5 to about 95 mole percent acrylamide and from about 5 to about 95 mole percent (meth)acrylic acid or a salt thereof, wherein the dispersion has a reduced specific viscosity from about 0.4 to about 40 dL/g.

11. The method of claim 1 wherein the cosmetically acceptable composition comprises a stable dispersion in an aqueous salt solution of a nonionic copolymer comprising from about 5 to about 95 mole percent acrylamide and from about 5 to about 95 mole percent vinyl acetate, wherein the dispersion has a reduced specific viscosity from about 0.4 to about 40 dL/g.

12. The method of claim 1 wherein the cosmetically acceptable composition comprises a stable dispersion in an aqueous salt solution of a cationic polymer comprising from about 20 to about 90 mole percent acrylamide and from about 80 to about 10 mole percent of one or more cationic monomers selected from the group consisting of diallyldimethylammonium chloride, dimethylaminoethyl acrylate methyl chloride quaternary salt and dimethylaminoethyl acrylate benzyl chloride quaternary salt, wherein the dispersion has a reduced specific viscosity from about 0.4 to about 30 dL/g.

* * * * *